(12) United States Patent
Zhang et al.

(10) Patent No.: US 12,079,381 B2
(45) Date of Patent: Sep. 3, 2024

(54) MOTION PLATFORM, HAPTIC FEEDBACK DEVICE AND HUMAN-COMPUTER INTERACTIVE SYSTEM

(71) Applicant: TENCENT TECHNOLOGY (SHENZHEN) COMPANY LIMITED, Shenzhen (CN)

(72) Inventors: Dongsheng Zhang, Shenzhen (CN); Lei Wei, Shenzhen (CN); Ke Chen, Shenzhen (CN); Qiang Li, Shenzhen (CN); Zhengyou Zhang, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 239 days.

(21) Appl. No.: 17/711,957

(22) Filed: Apr. 1, 2022

(65) Prior Publication Data

US 2022/0221931 A1 Jul. 14, 2022

Related U.S. Application Data

(63) Continuation of application No. PCT/CN2021/081114, filed on Mar. 16, 2021.

(30) Foreign Application Priority Data

Apr. 22, 2020 (CN) .......................... 202010320603.5

(51) Int. Cl.
*G06F 3/01* (2006.01)
*F16B 2/00* (2006.01)

(52) U.S. Cl.
CPC ................ *G06F 3/011* (2013.01); *F16B 2/00* (2013.01); *G06F 3/016* (2013.01)

(58) Field of Classification Search
CPC .... G06F 3/011; G06F 3/016; G06F 2203/012; F16B 2/00; G05G 5/03; G05G 9/04; A61B 34/76
See application file for complete search history.

(56) References Cited

U.S. PATENT DOCUMENTS

| 4,316,527 A | 2/1982 | Klaus |
| 6,061,004 A * | 5/2000 | Rosenberg .............. G06F 3/016 |
| | | 341/20 |

(Continued)

FOREIGN PATENT DOCUMENTS

| CN | 101104272 A | 1/2008 |
| CN | 101708609 A | 5/2010 |

(Continued)

OTHER PUBLICATIONS

Hadavand M. et al., "Design of a Force-Reflective Master Robot for Haptic Telesurgery Applications: RoboMaster1," 33rd Annual International Conference of the IEEE EMBS, Boston, Massachusetts USA, Aug. 30, 2011 4 pages.

(Continued)

*Primary Examiner* — William Lu
(74) *Attorney, Agent, or Firm* — ANOVA LAW GROUP PLLC

(57) ABSTRACT

This application discloses a motion platform, a haptic feedback device, and a human-computer interactive system. The motion platform includes a first platform, a second platform and a linkage assembly, the first platform and the second platform being connected by the linkage assembly, the second platform being configured to move relative to the first platform. The first platform comprises a first power take-off and a second power take-off, the first power take-off comprising a first output shaft and the second power take-off comprising a second output shaft. The linkage assembly comprises a first parallelogram linkage mechanism and a (Continued)

second parallelogram linkage mechanism connected to each other, and a two-bar linkage mechanism. The two-bar linkage mechanism and the first parallelogram linkage mechanism have the same plane of motion, and the second output shaft being configured to drive motion of the two-bar linkage mechanism.

20 Claims, 4 Drawing Sheets

(56) References Cited

U.S. PATENT DOCUMENTS

| | | | |
|---|---|---|---|
| 6,155,993 A * | 12/2000 | Scott | A61B 5/22 |
| | | | 600/595 |
| 9,804,724 B2 | 10/2017 | Colgate et al. | |
| 11,083,967 B1 * | 8/2021 | Summit | A63F 13/285 |
| 11,614,796 B1 * | 3/2023 | Summit | A63F 13/245 |
| | | | 345/633 |
| 2004/0024385 A1 * | 2/2004 | Stuart | B25J 9/1065 |
| | | | 606/1 |
| 2005/0183532 A1 * | 8/2005 | Najafi | B25J 17/0266 |
| | | | 74/490.01 |
| 2007/0236450 A1 * | 10/2007 | Colgate | G06F 3/041 |
| | | | 345/156 |
| 2009/0102620 A1 * | 4/2009 | Kato | G06F 3/011 |
| | | | 340/407.1 |
| 2009/0282331 A1 * | 11/2009 | Nagasaka | G06F 3/016 |
| | | | 715/701 |
| 2010/0275717 A1 | 11/2010 | Poyet et al. | |
| 2010/0300230 A1 * | 12/2010 | Helmer | B25J 9/106 |
| | | | 74/469 |
| 2015/0351857 A1 * | 12/2015 | Vander Poorten | B25J 18/007 |
| | | | 606/130 |
| 2020/0345553 A1 * | 11/2020 | Baudisch | G09B 21/003 |
| 2021/0096648 A1 * | 4/2021 | Summit | A63B 24/00 |

FOREIGN PATENT DOCUMENTS

| | | |
|---|---|---|
| CN | 102886777 A | 1/2013 |
| CN | 104015185 A | 9/2014 |
| CN | 104842342 A | 8/2015 |
| CN | 104924297 A | 9/2015 |
| CN | 105415350 A | 3/2016 |
| CN | 109664278 A | 4/2019 |
| CN | 109746900 A | 5/2019 |
| CN | 109955284 A | 7/2019 |
| CN | 111506197 A | 8/2020 |

OTHER PUBLICATIONS

European Patent Office European Search Report for Application No. 21792895.1-1224 Dec. 4, 2022 9 pages.
The State Intellectual Property Office of the People's Republic of China (SIPO) Office Action 1 for for 202010320603.Feb. 5, 2003, 2021 8 Pages (including translation).
The World Intellectual Property Organization (WIPO) International Search Report for PCT/CN2021/081114 May 26, 2021 6 Pages (including translation).
P.A. Millman et al., "Design of a Four Degree-Of-Freedom Force-Reflecting Manipulandum With a Specified Force/Torque Workspace," 1991 IEEE International Conference on Robotics and Automation, Apr. 1991. 6 pages.
3D System, Inc, "Haptic Devices," Retrieved from the Internet: URL: https://www.3dsystems.com/scanners-haptics#haptics-devices, retrieved on Mar. 14, 2022. 2 pages.

* cited by examiner

MOTION PLATFORM, HAPTIC FEEDBACK DEVICE AND HUMAN-COMPUTER INTERACTIVE SYSTEM

RELATED APPLICATIONS

This application is a continuation application of PCT Application No. PCT/CN2021/081114, filed on Mar. 16, 2021, which in turn claims priority to Chinese Patent Application No. 202010320603.5 and filed on Apr. 22, 2020. The two applications are incorporated herein by reference in their entirety.

FIELD OF THE TECHNOLOGY

This application relates to a motion platform, a haptic feedback device, and a human-computer interactive system.

BACKGROUND OF THE DISCLOSURE

With the continuous progress of science and technology, technologies such as virtual reality (VR) and augmented reality (AR) have been widely used. Technologies related to visual feedback has been developed, but there is great room for the development of haptic feedback technologies. The visual feedback technology can feedback a scene of a remote or virtual world to a user, and the haptic feedback technology can feedback the force of a remote or virtual world to a user. The combination of haptic feedback and visual feedback technologies can further enhance the user's sense of presence.

SUMMARY

Embodiments of this application provide a motion platform, a haptic feedback device, and a human-computer interactive system.

The motion platform includes a static platform, a dynamic platform, and a linkage assembly; the static platform and the dynamic platform being connected by the linkage assembly, and the static platform can drive motion of the dynamic platform through the linkage assembly, thereby transmitting a force of a remote or virtual world to the dynamic platform.

The haptic feedback device includes at least two motion platforms and a platform connection element connecting the at least two motion platforms. When a thumb and an index finger of a user are respectively placed on the dynamic platforms of the two motion platforms, through relative motion, the two dynamic platforms can realize the relative motion between the thumb and index finger such as pinching and rubbing, thereby transmitting the force of the remote or virtual world to the user and realizing haptic feedback. The motion platform and the haptic feedback device have characteristics of high stiffness, simple and compact structure, and good dynamic performance.

An embodiment of this application provides a motion platform, which includes a, a first platform, a second platform and a linkage assembly, the first platform and the second platform being connected by the linkage assembly, the second platform being configured to move relative to the first platform. The first platform comprises a first power take-off and a second power take-off, the first power take-off comprising a first output shaft and the second power take-off comprising a second output shaft. The linkage assembly comprises a first parallelogram linkage mechanism and a second parallelogram linkage mechanism connected to each other, and a two-bar linkage mechanism. The first parallelogram linkage mechanism and the second parallelogram linkage mechanism have a same or parallel planes of motion, the first parallelogram linkage mechanism being fixedly connected to the first output shaft, the second parallelogram linkage mechanism being fixedly connected to the second platform, and the first output shaft being configured to drive planar motion of the first parallelogram linkage mechanism and the second parallelogram linkage mechanism. The two-bar linkage mechanism and the first parallelogram linkage mechanism have the same plane of motion, one end of the two-bar linkage mechanism being fixedly connected to the second output shaft, the other end of the two-bar linkage mechanism being hinged with the second platform, and the second output shaft being configured to drive motion of the two-bar linkage mechanism.

An embodiment of this application further provides a haptic feedback device, which includes at least two motion platforms provided by the embodiments of this application and a platform connection element connecting the at least two motion platforms, each of the motion platforms being fixed on the platform connection element through the included first platform.

An embodiment of this application further provides a human-computer interactive system, which includes the haptic feedback device according to any of the foregoing and a control apparatus, the control apparatus being connected to the haptic feedback device and being configured to control motion of the haptic feedback device based on force information.

DESCRIPTION OF EMBODIMENTS

Figure 1:
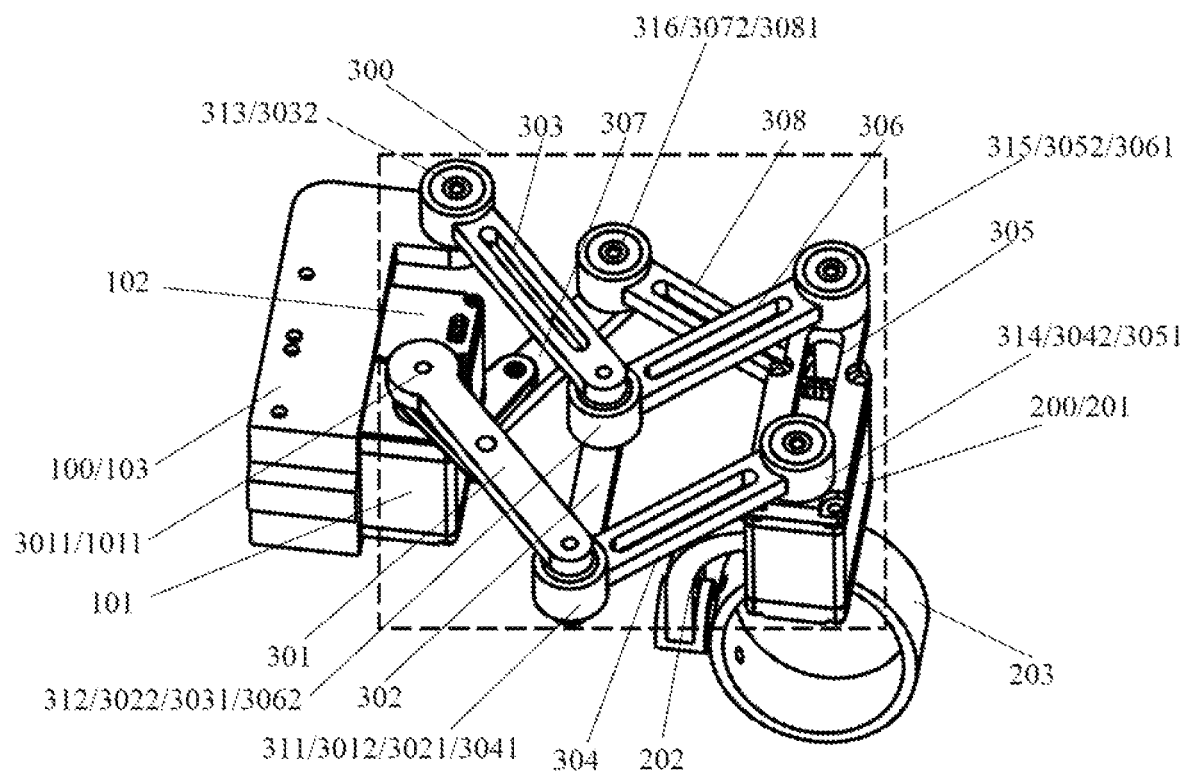
FIG. 1 is a schematic three-dimensional structural diagram of a motion platform provided by an embodiment of this application.

To make the objectives, technical solutions, and advantages of the embodiments of this application more comprehensible, the following clearly and completely describes the technical solutions in the embodiments of this application with reference to the accompanying drawings in the embodiments of this application. Apparently, the described embodiments are a part rather than all of the embodiments of this application. All other embodiments obtained by a person of ordinary skill in the art based on the embodiments of this application without creative efforts shall fall within the protection scope of this application.

Unless otherwise defined, a technical term or a scientific term used in this application is to have a general meaning understood by persons of ordinary skill in the art of this application. The "first", the "second", and similar terms used in this application do not indicate any order, quantity or significance, but are used to only distinguish different components. Similar terms such as "include" or "comprise" are intended to mean that an element or object appearing before the word covers the enumerated element or object appearing after the word and its equivalents, without excluding other elements or objects. Similar terms such as "connect" or "connected" are not limited to physical or mechanical connections, but may include electrical connections, whether direct or indirect. "Up", "down", "left", "right", or the like are used to only indicate a relative positional relationship, which may change accordingly when an absolute position of a described object is changed.

Embodiments of this application provide a motion platform, a haptic feedback device, and a human-computer interactive system. The motion platform includes a static platform, a dynamic platform, and a linkage assembly. The static platform and the dynamic platform are connected by the linkage assembly, and the static platform can drive motion of the dynamic platform through the linkage assembly, thereby transmitting the force of a remote or virtual world to the dynamic platform. The haptic feedback device includes at least two motion platforms and a platform connection element connecting the at least two motion platforms. When limbs of a user, such as a thumb and an index finger, are respectively placed on the dynamic platforms of the two motion platforms, through relative motion, the two dynamic platforms can realize the relative motion between the thumb and the index finger such as pinching and rubbing, thereby transmitting the force of the remote or virtual world to the user and realizing haptic feedback. In addition, the motion platform and the haptic feedback device have characteristics of high stiffness, simple and compact structure, and good dynamic performance.

The motion platform, the haptic feedback device, and the human-computer interactive system provided by the embodiments of this application are described in detail below with reference to the accompanying drawings.

In the embodiments of this application, the two or more components hinged with each other and a revolute joint formed by hinging described in the following indicate that the two or more components have a common rotation axis, and two or more components can rotate relatively around the common rotation axis.

Figure 2:
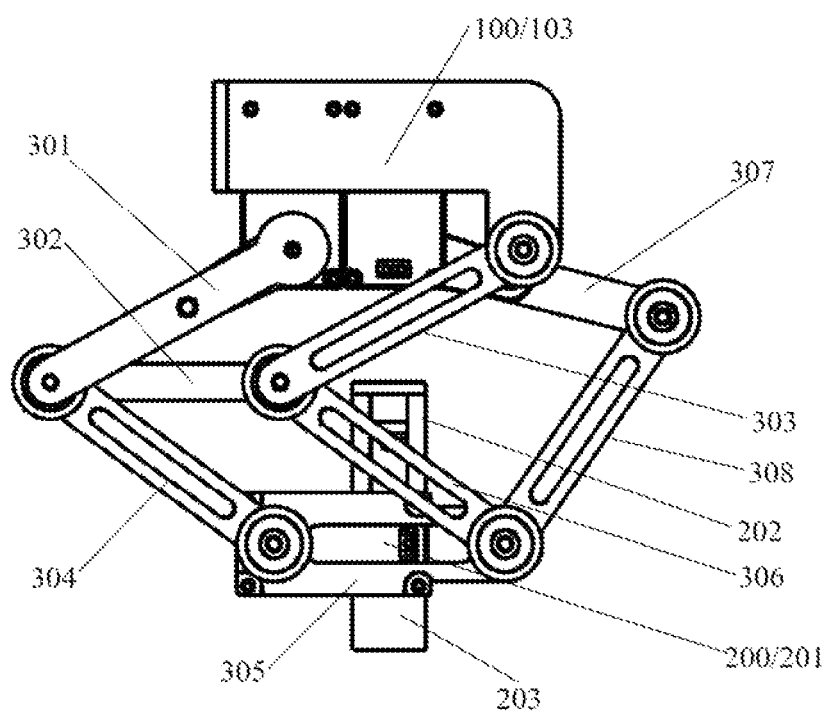
FIG. 2 is a schematic top structural view of the motion platform provided by the embodiment of this application.
Figure 3:
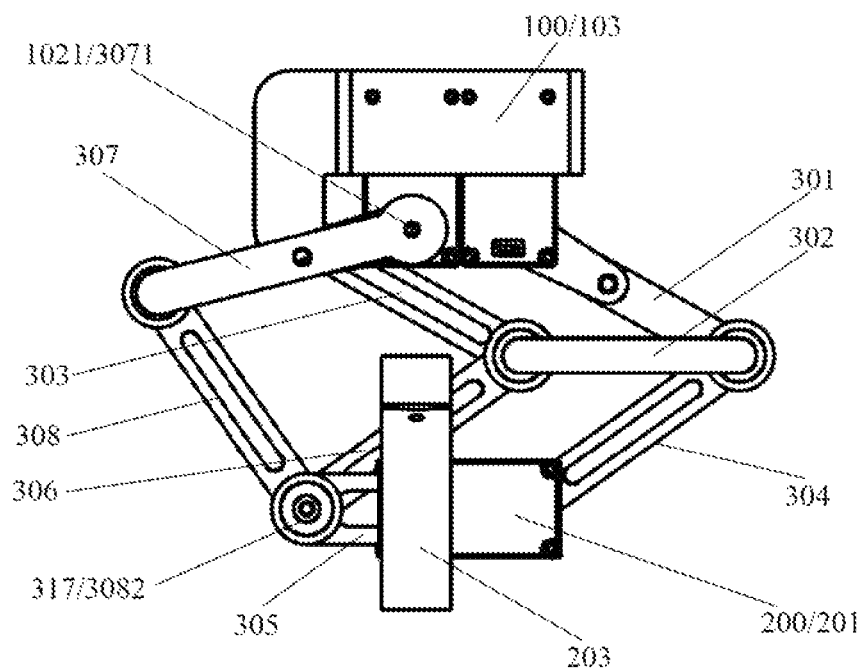
FIG. 3 is a schematic bottom structural view of the motion platform provided by the embodiment of this application.
Figure 4:
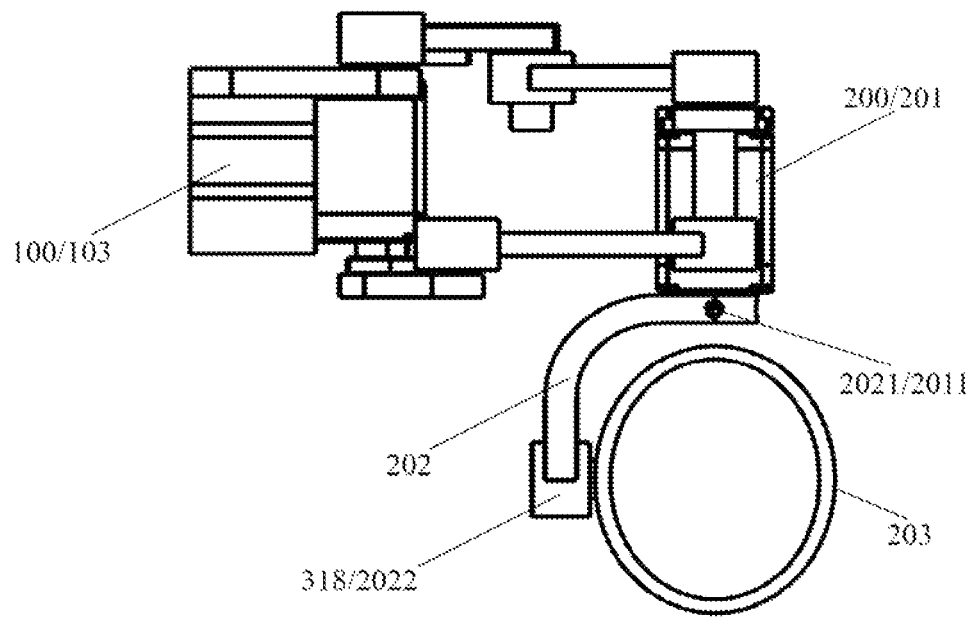
FIG. 4 is a schematic side structural view of the motion platform provided by the embodiment of this application.

FIG. 1 is a schematic three-dimensional structural diagram of a motion platform according to an embodiment of this application, FIG. 2 is a schematic top structural view of the motion platform, FIG. 3 is a schematic bottom structural view of the motion platform, and FIG. 4 is a schematic side structural view of the motion platform. As shown in FIGS. 1 to 4, the motion platform 10 provided by the embodiment of this application includes a static platform 100, a dynamic platform 200, and a linkage assembly 300 (as shown in the dotted block in FIG. 1). The static platform 100 and the dynamic platform 200 are connected by the linkage assembly 300, and the dynamic platform 200 can make planar motion relative to the static platform 100.

The "static platform" and "dynamic platform" are used herein to indicate that they can make relative motion to each other, and are not limited to the fact that the static platform must be in a static state and the dynamic platform must be in a moving state. Therefore, the static platform and the dynamic platform herein may also be referred to as a "first platform" and a "second platform" respectively.

As shown in FIGS. 1 to 4, the static platform 100 includes a mounting rack 103 on which a first power take-off 101 and a second power take-off 102 are fixedly provided. The first power take-off 101 includes a first output shaft 1011, and the second power take-off 102 includes a second output shaft 1021 (not shown in FIG. 1, see FIG. 3), and the first output shaft 1011 and the second output shaft 1021 are provided in parallel. For example, the first power take-off 101 and the second power take-off 102 are motors which can be connected to the mounting rack 103 by screws. Embodiments of this application do not limit the type of the motors, for example, the motors may be servo motors, stepping motors, or the like.

In some embodiments, as shown in FIGS. 1 to 4, the linkage assembly 300 includes a first parallelogram linkage mechanism, a second parallelogram linkage mechanism, and a two-bar linkage mechanism.

In some embodiments, as shown in FIGS. 1 to 4, the first parallelogram linkage mechanism and the second parallelogram linkage mechanism have same or parallel planes of motion, the first parallelogram linkage mechanism is fixedly connected to the first output shaft 1011, the second parallelogram linkage mechanism is fixedly connected to the dynamic platform 200, and the first output shaft 1011 is configured to drive the planar motion of the first parallelogram linkage mechanism and the second parallelogram linkage mechanism.

In some embodiments, as shown in FIGS. 1 to 4, a first turning point (a connection point between a first end 3011 of a first link 301 described in the following and the first output shaft 1011) of the first parallelogram linkage mechanism is fixedly connected to the first output shaft 1011, and a second turning point (a connection point between a second end 3032 of a third link 303 described in the following and the static platform 100) adjacent to the first turning point is hinged with the static platform 100. The first output shaft 1011 is configured to drive the planar motion of the first parallelogram linkage mechanism through the first turning point.

In some embodiments, as shown in FIGS. 1 to 4, the first parallelogram linkage mechanism and the second parallelogram linkage mechanism have same or parallel planes of motion. A first side (a second link 302 described in the following) of the second parallelogram linkage mechanism is connected to the first parallelogram linkage mechanism, and the first side of the second parallelogram linkage mechanism is parallel to a connecting line of the first turning point and the second turning point of the first parallelogram linkage mechanism (that is, the line connecting the first output shaft 1011 and the second output shaft 1021 on the plane of motion), and a second side (for example, a fifth link 305 shown later in FIG. 1) of the second parallelogram linkage mechanism parallel to the first side is fixedly connected to the dynamic platform 200.

Although in FIGS. 1 to 4 the first parallelogram linkage mechanism and the second parallelogram linkage mechanism share a same link (a second link 302 described in the following), the first parallelogram linkage mechanism and the second parallelogram linkage mechanism may not share the same link, which will be further described in the following.

In some embodiments, as shown in FIGS. 1 to 4, the two-bar linkage mechanism and the first parallelogram linkage mechanism have the same plane of motion, one end (a first end 3071 of a seventh link 307 described in the following) of the two-bar linkage mechanism is fixedly connected to the second output shaft 1021, the other end (a second end 3082 of an eighth link 308 described in the following) of the two-bar linkage mechanism is hinged with the second platform 200. The second output shaft 1021 is configured to drive the planar motion of the two-bar linkage mechanism.

In some embodiments, as shown in FIGS. 1 to 4, the linkage assembly 300 includes a first link 301, a second link 302, a third link 303, a fourth link 304, a fifth link 305, a sixth link 306, a seventh link 307, and an eighth link 308. A first end of 3011 of the first link 301 is fixedly connected to the first output shaft, a second end 3012 of the first link 301 is hinged with a first end 3021 of the second link 302 to form a first revolute joint 311, a second end 3022 of the second link 302 is hinged with a first end 3031 of the third link 303 to form a second revolute joint 312, and a second end 3032 of the third link 303 is hinged with the static platform 100 to form a third revolute joint 313. The first link 301, the second link 302, the third link 303, and a line connecting an axis of the first output shaft and an axis of the third revolute joint 313 form the first parallelogram linkage mechanism. The first power take-off 101 can drive the planar motion of the first parallelogram linkage mechanism, and an extension direction of the second link 302 remains unchanged during the motion.

In some embodiments, as shown in FIGS. 1 to 4, a first end 3041 of the fourth link 304 is hinged to the first revolute joint 311, and a second end 3042 of the fourth link 304 is hinged with a first end 3051 of the fifth link 305 to form a fourth revolute joint 314. A second end 3052 of the fifth link 305 is hinged with a first end 3061 of the sixth link 306 to form a fifth revolute joint 315. A second end 3062 of the sixth link 306 is hinged to the second revolute joint 312. The second link 302, the fourth link 304, the fifth link 305, and the sixth link 306 form the second parallelogram linkage mechanism. Thus, the second parallelogram linkage mechanism and the first parallelogram linkage mechanism share the second link 202, thereby reducing the number of revolute joints and simplifying the structure of the motion platform. The first parallelogram linkage mechanism can drive the planar motion of the second parallelogram linkage mechanism, and an extension direction of the fifth link 305 remains unchanged during the motion.

The first end 3041 of the fourth link 304 and the second end 3062 of the sixth link 306 may also be hinged at other positions. For example, the first end 3041 of the fourth link 304 is hinged at a middle portion of the first link 301, and the second end 3062 of the sixth link 306 is hinged at a middle portion of the third link 303. The middle portion refers to a certain part between two ends of a link, and is not limited to a midpoint position of the link. For another example, the first end and the second end of the second link 302 are respectively provided with extensions based on the structure shown in FIG. 1, the first end of the fourth link 304 is hinged on the extension of the first end of the second link 302, and the second end of the sixth link 306 is hinged on the extension of the second end of the second link 302. The foregoing hinged position of the first end 3041 of the fourth link 304 and the hinged position of the second end 3062 of the sixth link 306 also enable the planar motion of the second parallelogram linkage mechanism.

In some embodiments, as shown in FIGS. 1 to 4, the fifth link 305 is fixedly connected to the dynamic platform 200. Thus, because the extension direction of the fifth link 305 remains unchanged during the motion, the dynamic platform 200 can make translational motion in the plane of motion, but cannot make rotational motion.

In some embodiments, as shown in FIGS. 1 to 4, a first end 3071 of the seventh link 307 is fixedly connected to the second output shaft, a second end 3072 of the seventh link 307 is hinged with a first end 3081 of the eighth link 308 to form a sixth revolute joint 316, and a second end 3082 of the eighth link 308 is hinged with the dynamic platform 200 to form a seventh revolute joint 317 (not shown in FIG. 1, see FIG. 3). The seventh link 307 and the eighth link 308 form the two-bar linkage mechanism. Thus, the second power take-off 102 and the first power take-off 101 jointly drive the dynamic platform 200 to make the translational motion in the plane of motion, and can accurately control the position of the dynamic platform 200.

In some embodiments, the first end 3011 of the first link 301 is connected to the first output shaft of the first power take-off 101 by a flange, and the first end 3071 of the seventh link 307 is also connected to the second output shaft of the second power take-off 102 by a flange. Thus, the first power take-off 101 and the second power take-off 102 can respectively drive rotational motion of the first link 301 and the seventh link 307. Definitely, the first link and the first power take-off or the seventh link and the second power take-off may also be connected by other means such as a coupling, which is not limited in the embodiments of this application.

For example, the axis of the first output shaft 1011, the axis of the second output shaft 1021, and the axis of the third revolute joint 313 lie in the same plane. Such arrangement helps improve control accuracy of the first output apparatus and the second output apparatus on the position of the dynamic platform. Definitely, the axis of the first output shaft 1011, the axis of the second output shaft 1021, and the axis of the third revolute joint 313 may not lie in the same plane.

For example, an axis of the fourth revolute joint 314, an axis of the fifth revolute joint 315, and an axis of the seventh revolute joint 317 lie in the same plane. Such arrangement helps improve control accuracy of the first output apparatus and the second output apparatus on the position of the dynamic platform. For example, the axis of the fifth revolute joint 315 is coincident with the axis of the seventh revolute joint 317. Definitely, the axis of the fourth revolute joint 314, the axis of the fifth revolute joint 315, and the axis of the seventh revolute joint 317 may not lie in the same plane.

For example, as shown in FIGS. 1 to 4, the dynamic platform 200 includes a third power take-off 201, a first connection element 202, and a second connection element 203. One end of the first connection element 202 is fixedly connected to the third power take-off 201, and the other end of the first connection element 202 is hinged with a wall surface of the second connection element 203 to form an eighth revolute joint 318 (not shown in FIG. 1, see FIG. 4). The third power take-off 201 is configured to drive the first connection element 202 to rotate, and the rotation of the first connection element 202 drives the second connection element 203 to rotate. The second connection element 203 is rotatable relative to the first connection element 202 about an axis of the eighth revolute joint 318.

In some embodiments, as shown in FIGS. 1 to 4, the third power take-off 201 is a motor, which includes a third output shaft 2011 (not shown in FIG. 1, see FIG. 4). For example, the motor is connected to the fifth link 305 by a screw, and the motor may be a servo motor or a stepping motor. For example, the third output shaft 2011, the first output shaft 1011, and the second output shaft 1021 are arranged in parallel.

In some embodiments, as shown in FIGS. 1 to 4, the first connection element 202 has an approximately arc shape, a first end 2021 of the first connection element 202 is fixedly connected to the third output shaft 2011, and a second end 2022 of the first connection element 202 is hinged with the second connection element 203 to form the eighth revolute joint 318. An axis of the eighth revolute joint 318 is not parallel to an axis of the third output shaft 2011. For example, the axis of the eighth revolute joint 318 is perpendicular to or approximately perpendicular to the axis of the third output shaft 2011, for example, the difference between the included angle and the right angle is less than a preset angle threshold (for example, the preset angle threshold is 5°).

For example, the first end 2021 of the first connection element 202 is connected to the third output shaft 2011 of the third power take-off 201 by a flange. Thus, the third power take-off 201 can drive the rotational motion of the first connection element 202. Definitely, the first end 2021 of the first connection element 202 and the third output shaft 2011 of the third power take-off 201 may also be connected by other means such as the coupling.

In some embodiments, as shown in FIGS. 1 to 4, the second connection element 203 is ring-shaped and allows a human finger to extend in. For example, the second connection element 203 may be annular, elliptical or rectangular, and its specific shape is not limited in the embodiments of this application, as long as the second connection element 203 allows a finger to extend in and does not interfere with the first connection element 202 in motion.

The third power take-off 201 can drive the second connection element 203 to rotate through the first connection element 202, thereby increasing a degree of freedom of the second connection element 203 to enhance a haptic feedback effect. The second connection element 203 is hinged with the first connection element 202, which can further increase the degree of freedom of the second connection element 203 to enhance adaptability of the second connection element to the finger.

The motion platform provided by the embodiment of this application has characteristics of high stiffness, simple and compact structure, and good dynamic performance.

In the motion platform provided by the embodiment of this application, the linkage assembly has two translational degrees of freedom in the plane of motion, where the first link 301 and the seventh link 307 are driving links, and the other links are driven links. The first power take-off 101 drives the first link 301 to rotate, and the second power take-off 102 drives the seventh link 307 to rotate, and the first link 301 and the seventh link 307 drive other links to move, so as to realize motion control of the dynamic platform 200, thereby transmitting the force of the remote or virtual world to the dynamic platform.

In the motion platform provided by the embodiment of this application, the second connection element 203 has four degrees of freedom, which are two translational degrees of freedom following motion of the dynamic platform, a rotational degree of freedom following the first connection element 202 around the third power take-off 201, and a rotational degree of freedom around the axis of the eighth revolute joint 318.

When the user extends a finger into the second connection element of the dynamic platform, the dynamic platform drives the finger to move, thereby transmitting the force of the remote or virtual world to the user and realizing haptic feedback.

For example, as shown in FIG. 4, the motion platform provided by the embodiment of this application, in the axial direction of the first output shaft or the second output shaft (up and down direction in FIG. 4), the first link 301, the second link 302, the third link 303, the fourth link 304, the fifth link 305, and the sixth link 306 are located on the upper side, and the seventh link 307 and the eighth link 308 are located on the lower side. That is, the seventh link 307 and the eighth link 308 are located on a side of the first link 301, the second link 302, the third link 303, the fourth link 304, the fifth link 305, and the sixth link 306 that is closer to the second connection element 203. Such arrangement helps save space occupied by the motion platform.

In the axial direction of the first output shaft or the second output shaft, the seventh link 307 and the eighth link 308 may also be located on a side of the first link 301, the second link 302, the third link 303, the fourth link 304, the fifth link 305 and the sixth link 306 that is away from the second connection element 203.

For example, in the motion platform provided by the embodiment of this application, at least one bearing is provided in the first revolute joint 311. For example, the bearing is a rolling bearing, including an inner ring and an outer ring that can rotate relatively. The second end 3012 of the first link 301, the first end 3021 of the second link 302, and the first end 3041 of the fourth link 304 rotate relatively by using the bearing. Definitely, the first revolute joint 311 may also not include the bearing, and the second end 3012 of the first link 301, the first end 3021 of the second link 302, and the first end 3041 of the fourth link 304 rotate relatively by direct running fit. For example, the second revolute joint 312, the third revolute joint 313, the fourth revolute joint 314, the fifth revolute joint 315, the sixth revolute joint 316, the seventh revolute joint 317, and the eighth revolute joint 318 are in a structure similar to that of the first revolute joint 311.

Figure 5:
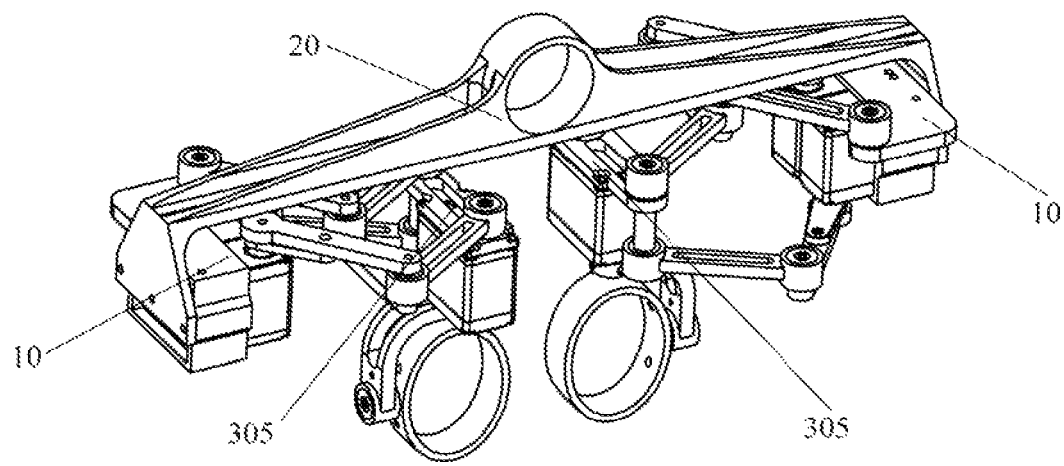
FIG. 5 is a schematic three-dimensional structural diagram of a haptic feedback device provided by an embodiment of this application.

An embodiment of this application further provide a haptic feedback device. FIG. 5 is a schematic three-dimensional structural diagram of the haptic feedback device provided by an embodiment of this application. For example, as shown in FIG. 5, the haptic feedback device provided by the embodiment of this application includes two motion platforms 10 and a platform connection element 20 connecting the two motion platforms.

For example, as shown in FIG. 5, the two motion platforms 10 are respectively connected to two ends of the platform connection element 20, and the two motion platforms 10 are disposed opposite each other. The two motion platforms 10 being disposed opposite each other means that the dynamic platforms 200 of the two motion platforms 10 are close to each other while the static platforms of the two motion platforms 10 are away from each other. That is, sides on which the dynamic platforms 200 are provided of the two motion platforms face each other, so that two fingers can be brought closer to each other or the fingers can be conveniently inserted into the second connection element.

For example, as shown in FIG. 5, the mounting racks 103 of the static platforms 100 of the two motion platforms 10 are fixedly connected to two ends of the platform connection element 20 by screws.

For example, the planes of motion of the dynamic platforms 200 of the two motion platforms 10 are approximately parallel to each other or in the same plane.

When a thumb and index finger (which may also be other fingers) of a user respectively extend into the second connection elements 203 of the two motion platforms 10, the second connection elements 203 of the two motion platforms make relative motion under the drive of the static platforms 100 and the dynamic platforms 200, so that the relative motion between the finger tip of the thumb and the finger tip of the index finger can be realized, thereby transmitting the force of the remote or virtual world to the user and realizing haptic feedback. For example, the second connection elements 203 of the two motion platforms get closer to or are separated from each other, so that contact (pinching) or separation motion between the finger tip of the thumb and the finger tip of the index finger can be achieved; the second connection elements 203 of the two motion platforms make relative motion to each other in a direction parallel to the extension of the fifth link 305, so that rubbing motion between the finger tip of the thumb and the finger tip of the index finger can be achieved.

Figure 6:
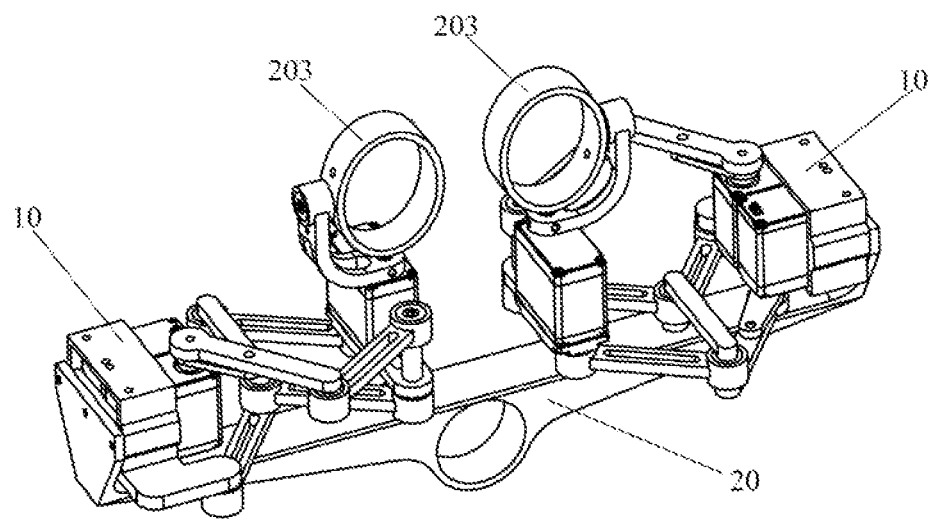
FIG. 6 is a schematic three-dimensional structural diagram of a motion state of a haptic feedback device provided by an embodiment of this application.
Figure 7:
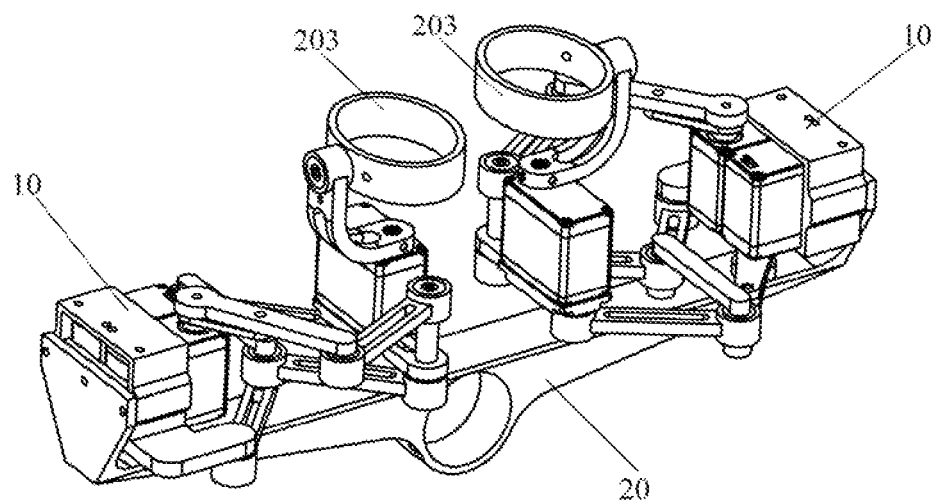
FIG. 7 is a schematic three-dimensional structural diagram of another motion state of a haptic feedback device provided by an embodiment of this application.

FIG. 6 is a schematic three-dimensional structural diagram of a motion state of the haptic feedback device, and FIG. 7 is a schematic three-dimensional structural diagram of another motion state of the haptic feedback device. FIG. 6 and FIG. 7 show different motion positions of the second connection element 203. As shown in FIG. 6, in this state, a central axis of the second connection element 203 is approximately parallel to a plane of motion of the linkage assembly. As shown in FIG. 7, in this state, the central axis of the second connection element 203 is perpendicular to or approximately perpendicular to the plane of motion of the linkage assembly, for example, the difference between the included angle and the right angle is less than a preset angle threshold (for example, the preset angle threshold is 5°).

In some embodiments, the haptic feedback device provided by the embodiments of this application may also include a greater number of motion platforms 10, so that the haptic feedback to more fingers can be achieved. The number of the motion platforms 10 is not limited in the embodiments of this application.

The haptic feedback device provided by the embodiment of this application also has characteristics of high stiffness, simple and compact structure, and good dynamic performance.

Figure 8:
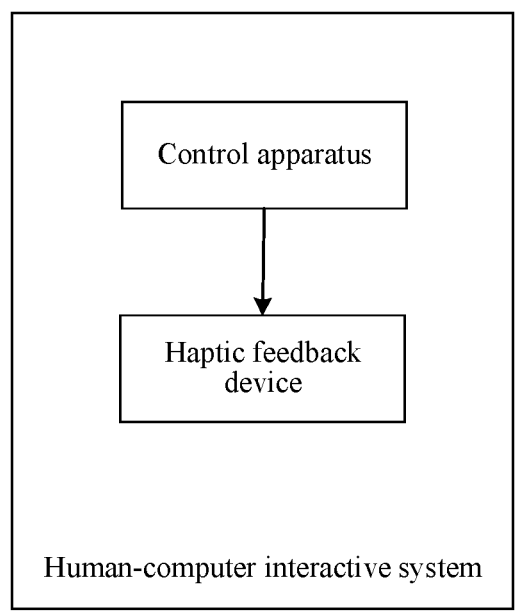
FIG. 8 is a schematic structural diagram of a human-computer interactive system provided by an embodiment of this application.

An embodiment of this application further provides a human-computer interactive system. FIG. 8 is a schematic structural of the human-computer interactive system. As shown in FIG. 8, the human-computer interactive system includes the haptic feedback device according to any one of the foregoing embodiments and a control apparatus. The control apparatus is connected to the haptic feedback device and is configured to control motion of the haptic feedback device based on force information, so as to feed back the force to a human and realize human-computer interaction. For example, the force information may be information stored in the control apparatus or received from a remote or virtual world.

For example, the control apparatus may be a computer or other apparatuses with a data processing function.

For example, the human-computer interactive system may also include a visual feedback device. The visual feedback device feeds back a picture of the remote or virtual world to a human through a display apparatus, so as to realize a visual feedback function.

In the human-computer interactive system provided by the embodiment of this application, by combining the haptic feedback technology and the visual feedback technology, a user can feel the force and see the picture, thereby enhancing a human-computer interactive effect.

For example, the human-computer interactive system may also include an audio feedback device. The audio feedback device feeds back a sound of the remote or virtual world to a human through a sounding apparatus, so as to realize an audio feedback function.

In the human-computer interactive system provided by the embodiment of this application, by combining the haptic feedback technology, the visual feedback technology, and the audio feedback technology, the user can feel the force, see the picture, and hear the sound, thereby enhancing the human-computer interactive effect.

For example, the human-computer interactive system can be implemented as a virtual reality (VR) or augmented reality (AR) device. For example, the human-computer interactive system can be applied to a game device, a wearable device, a robot, a mobile advertisement, an automobile, a medical instrument, or other devices with haptic and visual feedback functions.

The accompanying drawings of the embodiments of this application only relate to the structures related to the embodiments of this application, and for other structures, reference may be made the general design.

The embodiments of this application and features in the embodiments may be combined with each other in various embodiments.

The foregoing descriptions are merely specific implementations of this application, but are not intended to limit the protection scope of this application. Any variation or replacement that can be readily conceived of by a person skilled in the art within the technical scope disclosed in this application shall fall within the protection scope of this application. Therefore, the protection scope of this application shall be subject to the protection scope of the claims.

What is claimed is:

1. A motion platform, comprising a first platform, a second platform and a linkage assembly, the first platform and the second platform being connected by the linkage assembly, the second platform being a dynamic platform configured to move relative to the first platform being a static platform, wherein the first platform comprises a first power take-off and a second power take-off, the first power take-off comprising a first output shaft and the second power take-off comprising a second output shaft;

the linkage assembly comprises a first parallelogram linkage mechanism and a second parallelogram linkage mechanism connected to each other, and a two-bar linkage mechanism, wherein the first output shaft and the second output shaft are parallelly located on two opposite sides of the first platform;

the first parallelogram linkage mechanism and the second parallelogram linkage mechanism have a same or parallel planes of motion, the first parallelogram linkage mechanism being fixedly connected to the first output shaft, the second parallelogram linkage mechanism being fixedly connected to the second platform at a first side of the second platform, and the first output shaft being configured to drive planar motion of the first parallelogram linkage mechanism and the second parallelogram linkage mechanism; and the two-bar linkage mechanism and the first parallelogram linkage mechanism have the same plane of motion, one end of the two-bar linkage mechanism being fixedly connected to the second output shaft, the other end of the two-bar linkage mechanism being hinged with a second side of the second platform opposite to the first side, and the second output shaft being configured to drive motion of the two-bar linkage mechanism.

2. The motion platform according to claim 1, wherein a first turning point of the first parallelogram linkage mechanism is fixedly connected to the first output shaft, a second turning point adjacent to the first turning point is hinged with the first platform, and the first output shaft is configured to drive the planar motion of the first parallelogram linkage mechanism through the first turning point; and a first side of the second parallelogram linkage mechanism is connected to the first parallelogram linkage mechanism, and the first side is parallel to a target line, the target line being a line connecting the first turning point and the second turning point; a second side of the second parallelogram linkage mechanism is parallel to the first side, and the second side is fixedly connected to the second platform.

3. The motion platform according to claim 2, wherein the first parallelogram linkage mechanism comprises a first link, a second link and a third link, the second parallelogram linkage mechanism comprises a fourth link, a fifth link and a sixth link, and the two-bar linkage mechanism comprises a seventh link and an eighth link;

a first end of the first link and the first output shaft is fixedly connected at the first turning point, a second end of the first link is hinged with a first end of the second link to form a first revolute joint, a second end of the second link is hinged with a first end of the third link to form a second revolute joint, a second end of the third link is hinged with the first platform at the second turning point to form a third revolute joint, and the first link, the second link, the third link and a line connecting an axis of the first output shaft and an axis of the third revolute joint form the first parallelogram linkage mechanism;

a first end of the fourth link is hinged to the first revolute joint, a second end of the fourth link is hinged with a first end of the fifth link to form a fourth revolute joint, a second end of the fifth link is hinged with a first end of the sixth link to form a fifth revolute joint, a second end of the sixth link is hinged to the second revolute joint, the second link, the fourth link, the fifth link and the sixth link form the second parallelogram linkage mechanism, and the fifth link is fixedly connected to the second platform; and a first end of the seventh link is fixedly connected to the second output shaft, a second end of the seventh link is hinged with a first end of the eighth link to form a sixth revolute joint, a second end of the eighth link is hinged with the second platform to form a seventh revolute joint, and the seventh link and the eighth link form the two-bar linkage mechanism.

4. The motion platform according to claim 1, wherein the first output shaft and the second output shaft are arranged in parallel.

5. The motion platform according to claim 4, wherein the second platform comprises: a third power take-off, a first connection element, and a second connection element; wherein the third power take-off comprises a third output shaft;
a first end of the first connection element is fixedly connected to the third output shaft; and
the second connection element is hinged with a second end of the first connection element to form an eighth revolute joint, and an axis of the eighth revolute joint form an angle with an axis of the third output shaft.

6. The motion platform according to claim 5, wherein the third output shaft and the first output shaft are arranged in parallel.

7. The motion platform according to claim 5, wherein an axis of the eighth revolute joint is perpendicular to an axis of the third output shaft.

8. The motion platform according to claim 5, wherein the first power take-off, the second power take-off, and the third power take-off are motors.

9. The motion platform according to claim 3, wherein an axis of the first output shaft, an axis of the second output shaft, and an axis of the third revolute joint are in the same plane.

10. The motion platform according to claim 3, wherein an axis of the fourth revolute joint, an axis of the fifth revolute joint, and an axis of the seventh revolute joint are in the same plane.

11. The motion platform according to claim 10, wherein an axis of the fifth revolute joint is coincident with an axis of the seventh revolute joint.

12. The motion platform according claim 3, wherein in an axial direction of the first output shaft, the seventh link and the eighth link are located on a side of the first link, the second link, the third link, the fourth link, the fifth link and the sixth link that is closer to the second connection element.

13. A haptic feedback device, comprising at least two motion platforms, a platform connection element connecting the at least two motion platforms, each of the motion platforms being fixed on the platform connection element through a first platform, each of the motion platforms comprising the first platform, a second platform and a linkage assembly, the first platform and the second platform being connected by the linkage assembly, the second platform being configured to move relative to the first platform, the first platform being a static platform and the second platform being a dynamic platform, wherein:

the first platform comprises a first power take-off and a second power take-off, the first power take-off comprising a first output shaft and the second power take-off comprising a second output shaft;

the linkage assembly comprises a first parallelogram linkage mechanism and a second parallelogram linkage mechanism connected to each other, and a two-bar linkage mechanism, wherein the first output shaft and the second output shaft are parallelly located on two opposite sides of the first platform;

the first parallelogram linkage mechanism and the second parallelogram linkage mechanism have a same or parallel planes of motion, the first parallelogram linkage mechanism being fixedly connected to the first output shaft, the second parallelogram linkage mechanism being fixedly connected to the second platform at a first side of the second platform, and the first output shaft being configured to drive planar motion of the first parallelogram linkage mechanism and the second parallelogram linkage mechanism; and the two-bar linkage mechanism and the first parallelogram linkage mechanism have the same plane of motion, one end of the two-bar linkage mechanism being fixedly connected to the second output shaft, the other end of the two-bar linkage mechanism being hinged with a second side of the second platform opposite to the first side, and the second output shaft being configured to drive motion of the two-bar linkage mechanism.

14. The haptic feedback device according to claim 13, wherein, for each of the motion platforms, a first turning point of the first parallelogram linkage mechanism is fixedly connected to the first output shaft, a second turning point adjacent to the first turning point is hinged with the first platform, and the first output shaft is configured to drive the planar motion of the first parallelogram linkage mechanism through the first turning point; and a first side of the second parallelogram linkage mechanism is connected to the first parallelogram linkage mechanism, and the first side is parallel to a target line, the target line being a line connecting the first turning point and the second turning point; a second side of the second parallelogram linkage mechanism is parallel to the first side, and the second side is fixedly connected to the second platform.

15. The haptic feedback device according to claim 14, wherein, for each of the motion platforms, the first parallelogram linkage mechanism comprises a first link, a second link and a third link, the second parallelogram linkage mechanism comprises a fourth link, a fifth link and a sixth link, and the two-bar linkage mechanism comprises a seventh link and an eighth link;
   a first end of the first link and the first output shaft is fixedly connected at the first turning point, a second end of the first link is hinged with a first end of the second link to form a first revolute joint, a second end of the second link is hinged with a first end of the third link to form a second revolute joint, a second end of the third link is hinged with the first platform at the second turning point to form a third revolute joint, and the first link, the second link, the third link and a line connecting an axis of the first output shaft and an axis of the third revolute joint form the first parallelogram linkage mechanism;
   a first end of the fourth link is hinged to the first revolute joint, a second end of the fourth link is hinged with a first end of the fifth link to form a fourth revolute joint, a second end of the fifth link is hinged with a first end of the sixth link to form a fifth revolute joint, a second end of the sixth link is hinged to the second revolute joint, the second link, the fourth link, the fifth link and the sixth link form the second parallelogram linkage mechanism, and the fifth link is fixedly connected to the second platform; and
   a first end of the seventh link is fixedly connected to the second output shaft, a second end of the seventh link is hinged with a first end of the eighth link to form a sixth revolute joint, a second end of the eighth link is hinged with the second platform to form a seventh revolute joint, and the seventh link and the eighth link form the two-bar linkage mechanism.

16. The haptic feedback device according to claim 13, wherein, for each of the motion platforms, the first output shaft and the second output shaft are arranged in parallel.

17. The haptic feedback device according to claim 16, wherein, for each of the motion platforms, the second platform comprises: a third power take-off, a first connection element, and a second connection element; wherein
   the third power take-off comprises a third output shaft;
   a first end of the first connection element is fixedly connected to the third output shaft; and
   the second connection element is hinged with a second end of the first connection element to form an eighth revolute joint, and an axis of the eighth revolute joint form an angle with an axis of the third output shaft.

18. The haptic feedback device according to claim 17, wherein, for each of the motion platforms, the third output shaft and the first output shaft are arranged in parallel.

19. The haptic feedback device according to claim 17, wherein, for each of the motion platforms, an axis of the eighth revolute joint is perpendicular to an axis of the third output shaft.

20. A human-computer interactive system, comprising
   a haptic feedback device and a control apparatus, the control apparatus being connected to the haptic feedback device and being configured to control motion of the haptic feedback device based on force information;
   the haptic feedback device, comprising at least two motion platforms, a platform connection element connecting the at least two motion platforms, each of the motion platforms being fixed on the platform connection element through a first platform, each of the motion platforms, comprising the first platform, a second platform and a linkage assembly, the first platform and the second platform being connected by the linkage assembly, the second platform being configured to move relative to the first platform, the first platform being a static platform and the second platform being a dynamic platform, wherein:
   the first platform comprises a first power take-off and a second power take-off, the first power take-off comprising a first output shaft and the second power take-off comprising a second output shaft;
   the linkage assembly comprises a first parallelogram linkage mechanism and a second parallelogram linkage mechanism connected to each other, and a two-bar linkage mechanism, wherein the first output shaft and the second output shaft are parallelly located on two opposite sides of the first platform;
   the first parallelogram linkage mechanism and the second parallelogram linkage mechanism have a same or parallel planes of motion, the first parallelogram linkage mechanism being fixedly connected to the first output shaft, the second parallelogram linkage mechanism being fixedly connected to the second platform at a first side of the second platform, and the first output shaft being configured to drive planar motion of the first parallelogram linkage mechanism and the second parallelogram linkage mechanism; and
   the two-bar linkage mechanism and the first parallelogram linkage mechanism have the same plane of motion, one end of the two-bar linkage mechanism being fixedly connected to the second output shaft, the other end of the two-bar linkage mechanism being hinged with a second side of the second platform opposite to the first side, and the second output shaft being configured to drive motion of the two-bar linkage mechanism.

* * * * *